United States Patent [19]

Gross et al.

[11] Patent Number: 4,867,946
[45] Date of Patent: Sep. 19, 1989

[54] DEVICE FOR EVALUATING TEST STRIPS

[75] Inventors: Jürgen Gross, Hofheim am Taunus; Matthias Karger, Kriftel, both of Fed. Rep. of Germany

[73] Assignee: Hoechst Aktiengesellschaft, Frankfurt am Main, Fed. Rep. of Germany

[21] Appl. No.: 93,711

[22] Filed: Sep. 8, 1987

[30] Foreign Application Priority Data

Sep. 10, 1986 [DE] Fed. Rep. of Germany ....... 3630777

[51] Int. Cl.⁴ ............................................. G01N 21/01
[52] U.S. Cl. ....................................... 422/68; 422/58; 356/244
[58] Field of Search ........................ 422/65, 66, 68, 58; 436/44, 46, 47, 54, 168, 170; 356/432–435, 445, 446, 448, 213, 218, 234, 236, 244

[56] References Cited

U.S. PATENT DOCUMENTS

| 3,907,503 | 9/1975 | Betts et al. | 356/446 |
| 3,918,910 | 11/1975 | Soya et al. | 422/66 |
| 3,932,133 | 1/1976 | Ishikawa | 422/66 |
| 4,160,646 | 7/1979 | Furutani et al. | 436/44 |
| 4,279,514 | 7/1981 | Blümel et al. | 356/445 |
| 4,302,420 | 11/1981 | Jakubowicz et al. | 422/63 |
| 4,430,299 | 2/1984 | Horne | 422/64 |
| 4,552,458 | 11/1985 | Lowne | 356/446 |
| 4,659,229 | 4/1987 | Hernicz | 356/446 |
| 4,689,202 | 8/1987 | Khoja et al. | 422/65 |
| 4,780,283 | 10/1988 | Meinecke et al. | 422/58 X |

Primary Examiner—Michael S. Marcus
Assistant Examiner—Rebekah A. Griffith
Attorney, Agent, or Firm—Finnegan, Henderson, Farabow, Garrett & Dunner

[57] ABSTRACT

In the device for evaluating test strips having individual test sections, which consist of a terminal, a work platform with holder for the test strips and a sensing head, a position mark 5 is arranged for each test section 9 on the side of the holder 13. On the work platform 15, the sensing head 14 is arranged so as to be capable of of traversing the test sections 9 and the position marks 5. The sensing head 14 is provided with light sources 6, which are directed towards the test sections 9, of different wavelength and with a light receiver and with at least one position detector 10 which is directed towards the position marks.

1 Claim, 2 Drawing Sheets

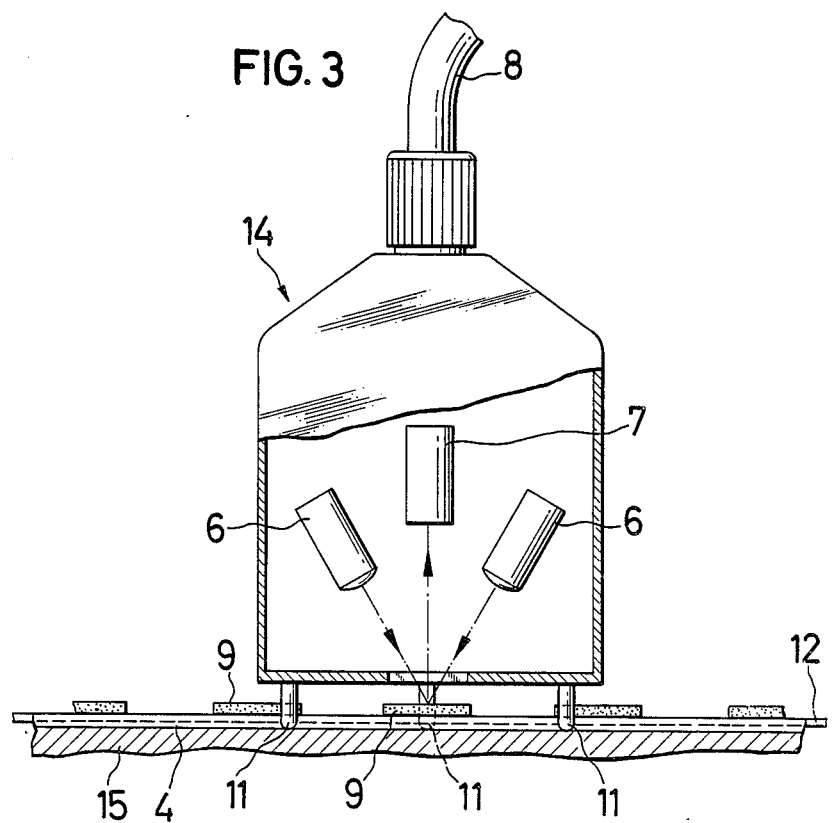

DEVICE FOR EVALUATING TEST STRIPS

DESCRIPTION

The invention relates to a device for evaluating test strips having individual test sections for medical tests, particularly of urine test strips, consisting of a terminal, a work platform with holder for the test strips, and a sensing head.

Test strips for determining bilirubin, urobilinogen, ketone bodies, ascorbic acid, glucose, protein, nitrite, the pH and the presence of blood are available for general urine diagnosis. Such test strips contain several test sections on which the reagents associated with the respective test are arranged as indicators. The test strips are moistened with urine and subsequently photometrically analysed.

Automatically operating multi-channel remission photometers are known which are used for analysing the test strips by means of defined light sources and light receivers. These highly differentiated photometers are particularly suitable for large-quantity investigations in chemical/medical test laboratories.

It is an object of the present invention to provide a device in modular construction which is suitable for economically investigating small members of test strips in medical practices and mobile facilities.

The object is achieved by a device of the type initially mentioned wherein a position mark is applied for each test section on the side of the holder, the sensing head is arranged so as to be capable of traversing the test sections and the position marks on the work platform, and the sensing head is provided with light sources of different wavelengths directed towards the test sections, and a light receiver and with at least one position detector directed towards the position marks.

On the work platform, guide grooves for the sensing head can be arranged on the side of the test strips and position marks, and the sensing head can be provided with at least three guide devices two of which engage a first guide groove and the third of which engages a second guide groove.

In the text which follows, the invention is explained in greater detail with the aid of drawings representing only one possible embodiment.

BRIEF DESCRIPTION OF THE DRAWINGS

FIG. 3 shows a side view in partial section of the work platform with sensing head.

Figure 2:
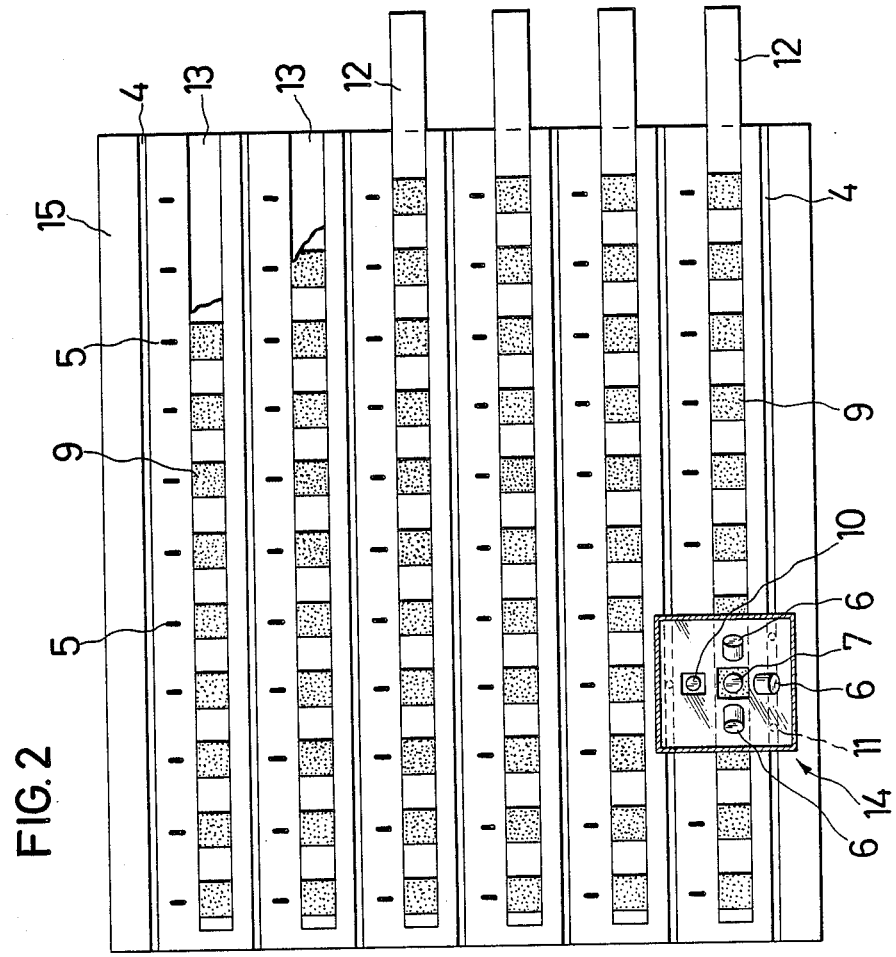
FIG. 2 shows a top view of the work platform with sensing head.
Figure 1:
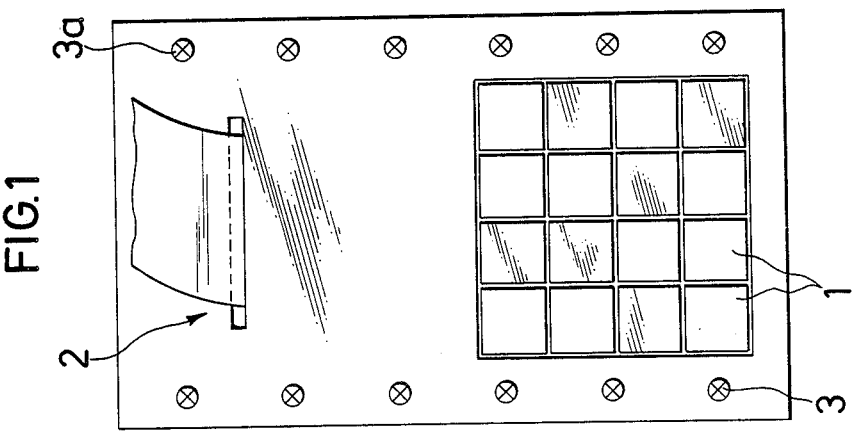
FIG. 1 shows a top view of the terminal.

Essentially, the terminal contains a processing device for the electric signals coming from the sensing head (14), a storage device, an operating device with keyboard (1), signal lamps (3, 3a), and a printer (2). Depending on the preprogramming, the green signal lamps are illuminated one after the other at intervals of, for example 10 seconds, in each case after taking the unit into operation. Each illumination of one of the green lamps indicates that a test strip (12) must be moistened with urine and deposited on the holder (13) which is associated with the signal lamp (3) illuminated at that time. As soon as the work platform (15) is filled with test strips (12), that is to say 60 seconds after the first green signal lamp (3) was illuminated in accordance with the program initially selected, the first red signal lamp (3a) is illuminated and indicates that the sensing head (14) must be moved over the first test strip. The 6 test strips are also traversed in the 10-second cycle. The sensing head (14) is connected to the terminal via a cable (8). It is equipped with up to 3 light sources (6) of different wavelength, at least one light receiver (7), and with at least one position detector (10). In addition, the sensing head can exhibit three guide devices (11). The work platform (15) has a holder (13) for the test strips (12). A position mark (5) is applied for each test section (9) on the side of the holder, and guide grooves (4) for the guide devices (11) of the sensing head (14) are arranged on the side of the test strips (12) and the position marks (5).

A maximum of two wavelengths per test section are stored and evaluated (for example comparison with stored calibration curves or tables). Thus, a maximum of 132 values are stored and evaluated for 6 test strips (12) which usually have 11 test sections (9). The results are displayed or, as shown, printed out. The work platform (15) can be cleaned and filled again. The terminal is calibrated in the usual manner by means of a standard gray-scale strip. Measuring range limits and/or calibration curves are entered by means of the keyboard (1). The dialog with the printer is carried out in the same manner. Position detection, functional checks and repeated measurement are also possible.

We claim:

1. A device for evaluating test strips having individual test sections, comprising:

a terminal;

a platform having a holder for holding a plurality of test strips aligned in rows;

a photometric sensing head having a plurality of light sources, each of a different wavelength, for directing light onto the test section of the test strip. said sensing head having a light receiver for receiving light reflected from said test section, and at least one position detecting means for determining the position of said sensing head relative said platform;

a plurality of position marks formed in rows on said platform, said marks being spaced from one another in each row by a predetermined distance corresponding to the spacing of adjacent test sections on said test strips;

a plurality of grooves formed in said platform, each groove extending substantially parallel to and between adjacent ones of said rows of position marks;

at least three guide pins projecting from the bottom of said sensing head for supporting the sensing head above the platform, said guide pins being positioned such that at least two of said guide pins removably engage with a respective one of said guide grooves and the remaining one of said guide pins removably engages with a guide groove adjacent said respective one of said guide grooves; and means for indicating when said position detecting means aligns with a respective one of said position marks, such alignment corresponding to a desired position of said light sources and said light receiver above a test section of a test strip.

* * * * *